(12) United States Patent
Markin

(10) Patent No.: US 8,822,224 B2
(45) Date of Patent: Sep. 2, 2014

(54) METHOD FOR AUTOMATIC TESTING OF ANATOMICAL LABORATORY SPECIMENS

(75) Inventor: Rodney S. Markin, Omaha, NE (US)

(73) Assignee: Prairie Ventures LLC, Omaha, NE (US)

( * ) Notice: Subject to any disclaimer, the term of this patent is extended or adjusted under 35 U.S.C. 154(b) by 910 days.

(21) Appl. No.: 12/166,437

(22) Filed: Jul. 2, 2008

(65) Prior Publication Data

US 2010/0004779 A1   Jan. 7, 2010

(51) Int. Cl.
*G06F 19/00* (2011.01)
*G01N 35/00* (2006.01)
*G01N 35/04* (2006.01)

(52) U.S. Cl.
CPC ...... *G01N 35/00584* (2013.01); *G01N 35/0092* (2013.01); *G01N 35/04* (2013.01); *G01N 2035/047* (2013.01)
USPC .......................................................... 436/43

(58) Field of Classification Search
CPC ............ G01N 35/00584; G01N 35/04; G01N 35/0092; G01N 2035/047
USPC .......................................................... 436/43
See application file for complete search history.

(56) References Cited

U.S. PATENT DOCUMENTS

| 5,351,801 A | 10/1994 | Markin |
| 5,366,062 A | 11/1994 | Markin |
| 5,370,215 A | 12/1994 | Markin |
| 5,377,813 A | 1/1995 | Markin |
| 5,402,875 A | 4/1995 | Markin |
| 5,417,922 A | 5/1995 | Markin |
| 5,427,743 A | 6/1995 | Markin |
| 5,510,984 A | 4/1996 | Markin |
| 5,529,166 A | 6/1996 | Markin |
| 5,562,202 A | 10/1996 | Newcomb |
| 5,567,386 A | 10/1996 | Markin |
| 5,589,137 A | 12/1996 | Markin |
| 5,614,415 A | 3/1997 | Markin |
| 5,876,670 A | 3/1999 | Mitsumaki et al. |

(Continued)

FOREIGN PATENT DOCUMENTS

| CA | 2152353 | 5/2005 |
| EP | 0676053 B1 | 8/1997 |

OTHER PUBLICATIONS

Online Dictionary Definition of the word, "Anatomic." Merriam-Webster, Apr. 28, 2011, 1 page.*
Cleveland Clinic Laboratories, "Anatomic Pathology Specimen Handling." Http://clevelandcliniclabs.com/reflab/SpeicmenHandling/AnatomicPathology/tabid/4250/default.aspx. Download Date: Oct. 18, 2011. Two pages.*

(Continued)

*Primary Examiner* — Christine T Mui
(74) *Attorney, Agent, or Firm* — Tyson B. Benson; Advent, LLP

(57) ABSTRACT

A method for automatic evaluation, processing and/or testing of an anatomic pathology specimen is disclosed. The specimen is placed into a primary or secondary container labeled with a unique identification code, placed into a specimen carrier, and the carrier marked with an identification code which uniquely identifies the specimen and, by virtue of the identification code, the evaluation, processing and/or tests to be conducted thereon. The identification code may be in the form of a bar code, an RFID tag or similar device or any other identification that is either human read able, machine readable or electronically transferred. The specimen contained within the specimen container or within the specimen carrier is entered into the anatomic pathology, histology or molecular diagnostics LAS at a receiving station, which reads the identification code.

14 Claims, 3 Drawing Sheets

(56) References Cited

U.S. PATENT DOCUMENTS

| | | | |
|---|---|---|---|
| 5,985,670 A * | 11/1999 | Markin | 436/47 |
| 6,117,683 A | 9/2000 | Kodama et al. | |
| 6,151,535 A | 11/2000 | Ehlers | |
| 7,212,127 B2 * | 5/2007 | Jacober et al. | 340/572.8 |
| 2004/0129769 A1 * | 7/2004 | Kovach | 235/375 |

OTHER PUBLICATIONS

Stratta, Robert et al., Experience with Protocol Biopsies After Solitary Pancreas Transplantation, Transplantation, vol. 60, No. 12, Dec. 27, 1995, pp. 1431-1437.*

J. Brooks Jackson, M.D., M.B.A.; Residency Training Program in Pathology; Johns Hopkins Medical Institutions, 11 pages.

\* cited by examiner

METHOD FOR AUTOMATIC TESTING OF ANATOMICAL LABORATORY SPECIMENS

BACKGROUND OF THE INVENTION

The present invention relates generally to anatomic pathology, histology and molecular diagnostic laboratory automation systems, and more particularly to an improved method for automating a laboratory for the evaluation, processing and/or testing of individual surgical pathology specimens, cytology specimens, autopsy specimens, histology specimens, molecular diagnostics/genetics specimen and any other specimen or part that is submitted to the anatomic pathology laboratory or laboratories.

Clinical laboratory and anatomic pathology, histology and molecular diagnostic evaluation, processing and/or testing has changed and improved remarkably over the past 100 years. Initially, and anatomic pathology, histology and molecular diagnostic evaluation, processing and/or tests or assays were performed manually, and generally utilized large quantities of serum, blood, tissues or other materials/body fluids. As mechanical technology developed in the industrial work place, similar technology was introduced into the clinical laboratory. With the introduction of new technology, methodologies were also improved in an effort to improve the quality of the results produced by the individual instruments and devices, and to minimize the amount of specimen required to perform each anatomic pathology, histology and molecular diagnostic evaluation, processing and/or test.

More recently, instruments have been developed to increase the efficiency of evaluation, processing and/or testing procedures by reducing turn around time and decreasing the volumes of biological tissues and materials necessary to perform various evaluations and/or assays. Present directions in laboratory and anatomic pathology, histology and molecular diagnostic evaluation, processing and/or testing focus on cost containment procedures and instrumentation. Anatomic pathology, histology and molecular diagnostic laboratory automation is one area in which cost containment procedures are currently being explored and refined. Robotic engineering and specimen processing has evolved to such a degree that various types of robotic devices have been applied in the clinical laboratory and anatomic pathology, histology and molecular diagnostic settings.

The main focus of prior art anatomic pathology, histology and molecular diagnostic laboratory automation relies on the implementation of automated processing devices for tissue processing, staining and cover slip application to stained or processed glass slides and systems to connect the specimen handling and information needs of the anatomic pathology, histology and molecular diagnostic laboratories. Known systems in the anatomic pathology, histology and molecular diagnostic laboratory setting utilize separate automated processing devices connected by conveyor segments to move specimens from processing station to processing station. In order to obtain cost savings, the specimens are sorted manually, and grouped to be conveyed to a specific location. In this way, a carrier or person will move a group of 5-20 specimens from the processing location to the specific workstation to perform a single evaluation, process and/or test, or a battery of evaluations. Processes and/or tests, on each of the specimens delivered.

While grouping a plurality of specimens in a single carrier may be more cost efficient where every specimen requires only a single specific anatomic pathology, histology and molecular diagnostic test, and none of the specimens within a carrier require special priority, it is not uncommon in the hospital environment for a specimen to be subjected to a variety of different evaluations, processes and/or tests, or for a particular specimen to require a very short turn-around time (stat evaluation, processing and/or testing). In such an event, the prior art automation systems may not be effectively or efficiently utilized, and the particular specimen would have to be manually moved to various work or processing stations or locations based upon the time constraints and evaluations, processes and/or tests designated for the specimen directed by a person or group of people.

Another problem with prior attempts at anatomic pathology, histology and molecular diagnostic laboratory automation is in tracking the specimen and reporting the results of the specimen evaluated, processed and/or tested. Results can serve as the basis for requiring additional evaluation, processing and/or testing of a particular specimen. If the evaluation, processing and/or testing is required within a short time period, rapid and efficient reporting of results can improve patient care quality and efficiency as well as laboratory quality and efficiency.

SUMMARY OF THE INVENTION

It is a general object of the present invention to provide a method for automating an anatomic pathology, histology and molecular diagnostic laboratory which permits individual and independent assignment of a specimen, including any part or subpart thereof, to one or more of a plurality of workstations within the laboratory.

Another object of the present invention is to provide a method for automating an anatomic pathology, histology and molecular diagnostic clinical laboratory which can prioritize individual specimens to improve turn around time for the evaluation, processing and/or testing of an individual specimen.

A further object is to provide a method for automating an anatomic pathology, histology and molecular diagnostic laboratory which determines optional routing to a particular workstation, and detects any time delays because of other specimens present in a queue at a workstation.

An additional object is to provide a method of automating a anatomic pathology, histology and molecular diagnostic laboratory wherein the tracking and transportation are independent of the mechanism; i.e., people, automated guided vehicles and conveyor systems may be used interchangeably.

Still another object of the present invention is to provide a method for automating a anatomic pathology, histology and molecular diagnostic clinical laboratory which tracks a specimen location throughout the laboratory and reports evaluation, processing and/or test results to a central database for immediate review by a physician.

These and other objects will be apparent to those skilled in the art.

The method for automatic testing of an anatomic pathology, histology and molecular diagnostic laboratory specimen of the present invention includes the initial step of obtaining a specimen to be evaluated, processed and/or tested and placing the specimen into a specimen container. Information regarding the specimen and any evaluation, processing and/or testing to be conducted thereon is entered into a computerized laboratory information system (LIS), an anatomic pathology information system (APIS) or Electronic Health Record (EHR) ordering system which is connected to and communicates with any or all parts of an anatomic pathology, histology or molecular diagnostics laboratory automation system (LAS) software. The specimen container is inserted in a specimen carrier, and the carrier marked with an identification code which uniquely identifies the specimen and, by virtue of the identification code, the evaluations, processing and/or tests to be conducted thereon. The specimen contained within the specimen carrier is entered into the LAS at a receiving station, which reads the identification code and thereby determines:

1. If evaluation, processing and/or tests which require process/steps which can run at variety of workstations;
2. If evaluation, processing and/or tests can have certain steps merged in an effort to ensure that they are carried out properly;
3. The priority of the specimen relative to other specimens already in the LAS;
4. The priority of each evaluation, processing and/or test to be conducted on the specimen; and
5. The most direct route from their receiving station to the workstation for conducting the highest priority evaluation, processing and/or test on the specimen.

The specimen is then entered into the LAS either by electronic registration into the system alone or by physical entry into one or more components of the automation system with electronic registration at the point of entry into the system or device. The LAS software will operate a communication and/or a control linkage to the appropriate workstation to direct the function of the evaluation, process and/or testing at the workstation. Upon directing the specimen to the appropriate workstation, the anatomic pathology, histology or molecular diagnostics LAS software recalculates the priority of all specimens in the LAS. After completion of an evaluation, process and/or test, a specimen is returned to the transport media of the LAS and directed to any subsequent workstations for other evaluation, process and/or testing, or to an archiving station for temporary or permanent storage or disposal of the specimen.

DETAILED DESCRIPTION OF THE INVENTION

Figure 1:
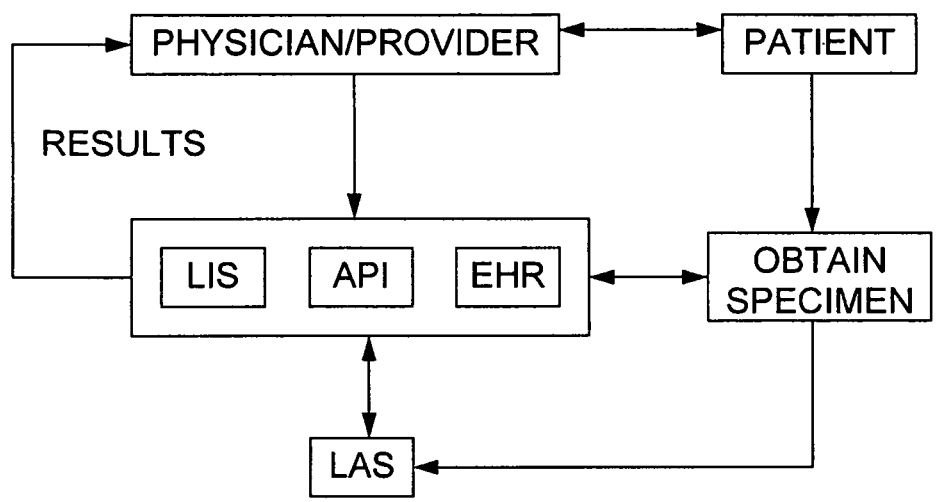
FIG. 1 is a flow chart showing the integration of a anatomic pathology, histology or molecular diagnostics laboratory automation system with a computerized laboratory information system (LIS), an anatomic pathology information system (APIS) or Electronic Health Record (EHR) ordering system which is connected to and communicates with any or all parts of an anatomic pathology, histology or molecular diagnostics laboratory automation system (LAS) software.

Referring now to the drawings, FIG. 1 is a flowchart showing how the anatomic pathology, histology or molecular diagnostics laboratory automation system (LAS) of the present invention integrates with the day-to-day operations of a hospital or health care system. Box 10 refers to any patient who is in need of examination, process and/or diagnosis. Box 12 represents the relevant physician(s) or other practitioner(s) or provider(s) who will interpret the results of the examination in order to determine the necessity of examination, process and/or tests and the priority level to be given various required examinations, processes and/or tests, in order to make a final diagnosis and/or prescribe a specified treatment. Information passes in both directions between physician/provider and patient during this episode of care.

As a result of the examination, the Physician/Provider will make a record of the examination results, and may enter a request for a specific evaluation, process and/or test(s) to be performed and designate the priority level of such examination, process and/or test(s). This information is entered into the computerized laboratory information system (LIS), an anatomic pathology information system (APIS) or Electronic Health Record (EHR) ordering system which is connected to and communicates with any or all parts of an anatomic pathology, histology or molecular diagnostics laboratory automation system (LAS) software shown as box 14 in the flowchart. The LIS/APIS/EMR will correlate patient information, room information, as well as any insurance or other typical general information necessary for operation of a health care system or hospital. The EMR is an information system which communicates with various information systems of the health care system to integrate all functions of the health care system/hospital.

Once the physician/provider's order is correlated with the patient identification information, the EMR will forward the correlated information to the laboratory information system (LIS) and/or the anatomic pathology information system (APIS) designated as box 16 in the FIG. 1. The LIS and/or the APIS is an information system which may be connected to the EMR to quickly and efficiently communicate information.

As shown in FIG. 1, the computerized laboratory information system (LIS), an anatomic pathology information system (APIS) or Electronic Health Record (EHR) ordering system which is connected to and communicates with any or all parts of an anatomic pathology, histology or molecular diagnostics laboratory automation system (LAS) software assigns the task of obtaining a specimen to an appropriate technician, the retrieval/reception of the specimen, being designated generally at box 18. The physical specimen(s), sample obtained from the patient is then entered in the laboratory automation system (LAS) designated generally as box 20. The LAS takes the place of prior art manual evaluation, processing and/or testing procedures, including the reporting of the evaluation results to the computerized laboratory information system (LIS), an anatomic pathology information system (APIS) or Electronic Health Record (EHR) ordering system. The LIS, APIS and/or EHR, communicates with the LAS to order specific evaluations, processes and/or tests related to a specific specimen, and receive the results of those evaluations. The computerized laboratory information system (LIS) or an anatomic pathology information system (APIS) may also communicate with the Electronic Health Record (EHR) to report evaluation results for accounting and insurance purposes. The computerized laboratory information system (LIS) or an anatomic pathology information system (APIS) reports either to the physician/provider via a separate workstation, or via the EHR, to report the results of the requested evaluation.

Figure 2:
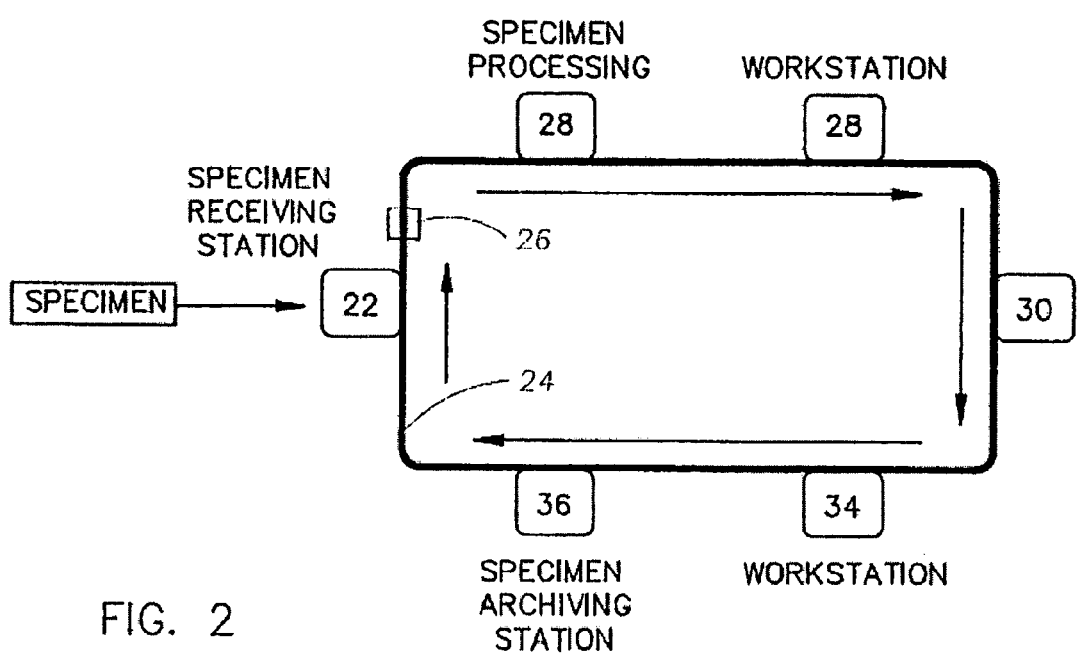
FIG. 2 is a schematic diagram of specimen movement through a anatomic pathology, histology or molecular diagnostics laboratory automation system.

Referring now to FIG. 2, a schematic diagram of specimen/specimen carrier movement throughout the LAS is shown. The specimen arrives at a specimen receiving/accessioning station 22, where the specimen is entered on a conveyor system designated generally at 24. During the assignment of the task of obtaining a specimen, the computerized laboratory information system (LIS) or an anatomic pathology information system (APIS) may also provide a specimen container marked with an appropriate patient identification code. The inventor has found that a conventional bar code label applied to the specimen container is a simple and efficient method for fulfilling this function. Anatomic pathology, histology and molecular diagnostic specimen containers are not all designed for transport in a transportation mechanism therefore, a separate carrier 26 may provided to support an individual specimen container in a transportation mechanism 24. At specimen receiving station 22, the carrier 26 is given an identification code which correlates through the LAS software with the specimen container and the specimen to be evaluated, processed and/or tested, so that the container and carrier may be directed throughout the laboratory automation system, even when the specimen container is removed from the carrier for specific testing at a workstation (i.e. paraffin embedding workstation).

As shown in FIG. 2, transportation mechanism 24 is preferably a continuously moving transportation mechanism which will move carriers 26 in a closed loop system. At receiving station 22, the carrier identification is entered into the LAS to determine which workstations the specimen must utilize, the order in which the stations are to be utilized, the priority of the particular evaluations, processes and/or tests to be conducted or steps to be taken, and any other pertinent information with respect to priority or turn around time. Entry of this information may be as simple as scanning the bar code or RFID tag of the specimen or carrier with the appropriate machine reader.

While FIG. 2 shows only 4 specific workstations, 28, 30, 32, and 34, obviously a conventional anatomic pathology laboratory could have a wide variety of such stations throughout a facility. The closed loop system of the transportation mechanism 24 permits a specimen to stop at any given workstation in a predetermined geographic location. Thus, if time constraints require that the evaluation, process and/or test of workstation 34 be performed first, and that an evaluation, process and/or test of workstation 32 be performed at some time after the evaluation, process and/or test of workstation 34, the specimen can travel on the transportation mechanism 24 past workstations 30 and 32, directly to workstation 34, for immediate and evaluation, processing and/or testing. Carrier 26 is then reintroduced into the transportation mechanism 24 to follow the closed loop around to the next workstation assigned to the specimen. Once the testing has been completed, the specimens are forwarded to the specimen archiving station 36 for removal from transportation mechanism 24 and appropriate storage.

Figure 3:
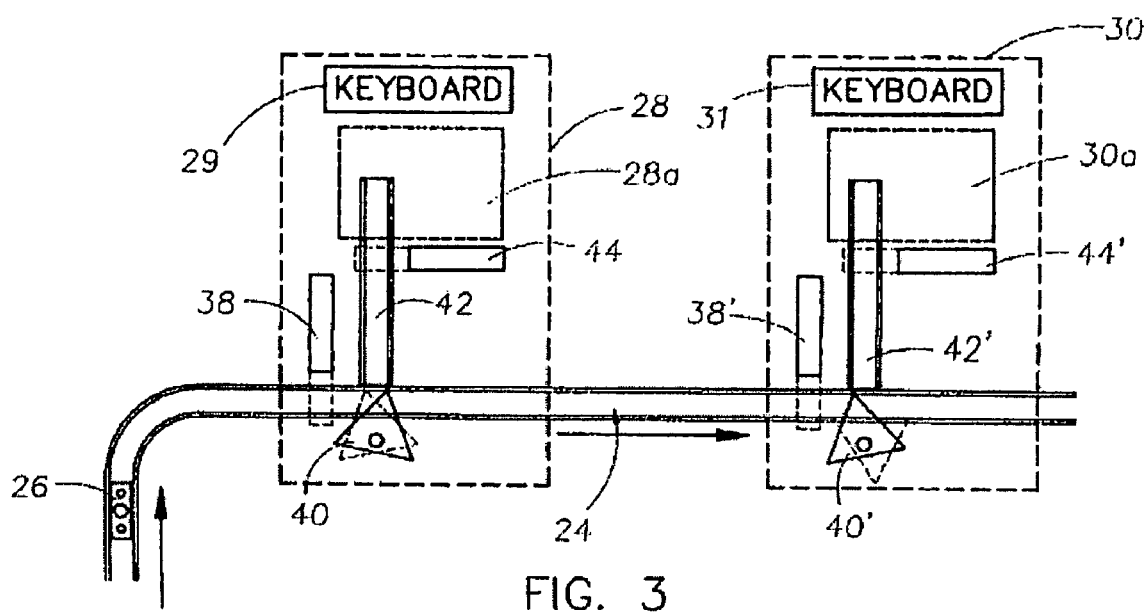
FIG. 3 is an enlarged schematic view of the specimen processing station and one workstation along the schematic of FIG. 2.

Referring now to FIG. 3, an enlarged view of a portion of the schematic of FIG. 2 is shown. Workstations 28 and 30 are shown in schematic view to demonstrate portions of the method for detecting and routing specimens at each specific workstation located along transportation mechanism 24. As carrier 26 moves along transportation mechanism 24, it will pass within the zone of workstation 28 where a sensor 38 will detect the identification code on carrier 26. In the preferred embodiment of the invention, sensor 38 is a bar code reader or RFID reader while the identification code on the carrier 26 is a bar code or RFID tag. Sensor 38 is connected with the LAS, to record the movement of carrier 26, and determine routing of the carrier.

A gate 40 is connected to the LAS and will be activated to redirect the movement of carrier 26 off of conveyor 24 and on to an auxiliary conveyor 42 to reach the entry point 28*a* within the workstation 28. Testing area 28*a* may be comprised of manual testing, fully automatic mechanical testing, or partially automated testing. An additional sensor 44 is positioned along auxiliary transportation mechanism 42 to track the location of the carrier and specimen, and may be utilized to activate any automatic mechanical equipment associated with the workstation 28*a*.

As discussed above, the software of the LAS will direct the movement of the specimen or specimen to the appropriate workstation at the appropriate time. A keyboard 46, or the like, is provided at each workstation to enter test results into the computerized laboratory information system (LIS) or an anatomic pathology information system (APIS), which in turn distributes the appropriate instructions to the pertinent sensors and workstations, as described in more detail herein below. Once testing has been completed, the specimen or specimen is again placed in into the LAS system 24 by auxiliary transportation mechanism 42.

If the particular test requested by the physician/provider is performed at workstation 30, then the receiving station input 22 will allow the LAS software to determine the optimal route to workstation 30, while simultaneously determining the priority of the requested evaluation, process and/or test for carrier 26 relative to other specimen carriers in the system along the transportation mechanism 24. Sensors 38 at each gate 40 of each workstation serve to detect the relative location of the carrier as well as the states of the gate 40 of the workstation. Each sensor 44 detects the presence of a carrier at the entry point of the particular workstation, as well as the number of other carriers which are queued in line for evaluation, processing and/or testing at the particular workstation.

In this example, sensor 38' will acknowledge the passage of carrier 26 thereby, thereby triggering the LAS to direct gate 40' to divert the carrier 26 onto the auxiliary transportation system 42' of workstation 30. A sensor 34' will then direct the specimen to the appropriate testing area 30*a*.

Once the carrier has been directed into the queue of workstation 30, the priority table of all carriers in the LAS is recalculated to again direct the next highest priority specimen along the optimal route to the requested workstation.

Once the test performed by workstation 30 has been completed, the results are transmitted from the work area 30*a* to the computerized laboratory information system (LIS) or an anatomic pathology information system (APIS) by virtue of keyboard 46', and the specimen is loaded in the specimen carrier 26 and positioned on auxiliary transportation mechanism 42'. The priority of any subsequent testing is then recalculated in the LAS priority table. The specimen will then be moved to the main transportation mechanism 24 for movement to the next appropriate station.

Workstations 32 and 34 are not shown in detail, but include the same basic equipment as workstations 28 and 30. Thus, a sensor 38' located at workstations 32 and 34 will acknowledge passage of the specimen at that location and either direct the specimen into the workstation, or direct the specimen to continue past the workstation. If the order in which the evaluations, processes and/or tests are conducted is important, the specimen can be directed to bypass any workstation along the transportation mechanism 24 so as to immediately reach the highest priority workstation to perform the appropriate testing. Since the transportation mechanism is a closed loop, the specimen can then be moved around the loop to any other workstation.

Once all requested tests have been performed, the specimen will be directed into the specimen archiving station utilizing a sensor 38' and gate 40' in the same manner as workstations 28, 30, 32 and 34. Since every sensor 38, 38', 44 and 44' is interconnected by way of the LAS software, the location and status of any specimen or specimen is always readily accessible by the physician/provider. Since the computerized laboratory information system (LIS), an anatomic pathology information system (APIS) or Electronic Health Record (EHR) ordering system is programmable, the physician/provider can call for additional evaluations, processes and/or tests at any time during the movement of the specimen within the LAS. This ability to direct an individual specimen to one or more of a plurality of workstations decreases the turn around time and increases the versatility of the automation system. With the use of robotics, and fully integrated laboratory instrumentation, it is possible to fully automate the process of anatomic pathology specimen handling, processing and evaluation.

The results of standard testing may conventionally require additional testing. In such a case, the LIS may automatically assign additional or different workstation stops based upon the results received from an evaluation, processing and/or test at any given workstation. The capability of prioritizing the evaluation, processing and/or testing also permits a physician to diagnose and/or otherwise individualize the test battery which is required for an individual patient and/or the individual patient's specimen.

Whereas the invention has been shown and described in connection with the preferred embodiment thereof, it will be understood that many modifications, substitutions and additions may be made which are within the intended broad scope of the appended claims. There has therefore been shown and described an improved method for automatic evaluation, processing and/or testing of an anatomic pathology, histology and molecular diagnostic specimen.

What is claimed is:

1. A method for routing a specimen through an automated anatomic pathology, histology and molecular diagnostic laboratory system, comprising the steps of:
    entering a first specimen to be evaluated, processed and/or tested in a specimen container;
    inputting information regarding the specimen and the evaluation, processing and/or testing to be conducted on the specimen into at least one of a computerized laboratory information system (LIS), an anatomic pathology information system (APIS) or an Electronic Health Record (EHR) ordering system, which is connected to and communicates with at least part of an anatomic pathology, histology or molecular diagnostics laboratory automation system (LAS) software;
    marking a first carrier and/or specimen with an identification code identifying the first specimen and the evaluation, processes and/or tests to be conducted thereon, the processes comprising a paraffin embedding process;
    placing the first specimen in the first carrier and entering the first carrier into the LAS at a receiving station;
    reading the identification code and calculating:
    the priority of the first specimen relative to any other specimens entered into the LAS;
    the priority of each test to be conducted on the first specimen thereof relative to one another; and
    the most direct route from the receiving station to a first paraffin embedding workstation for conducting the paraffin embedding process;
    entering the first carrier into the LAS by directing the carrier onto a transportation mechanism or modality of the LAS, the transportation mechanism or modality extending among a plurality of workstations, each workstation adapted to conduct a predetermined test;
    managing the transportation mechanism or modality to direct the first carrier and/or specimen to the first paraffin embedding workstation, the first paraffin embedding workstation disposed along the transportation mechanism;
    operating a gating mechanism at the first paraffin embedding workstation to direct the carrier to a workstation auxiliary transportation mechanism or conveyor, for embedding the specimen in paraffin; and
    recalculating the priority of the first specimen and any other specimens operating within the LAS upon directing of the first carrier or specimen to the first paraffin embedding workstation.

2. The method of claim 1, further comprising the steps of:
    conducting the paraffin embedding after the step of directing the first carrier or specimen to the first workstation auxiliary transportation mechanism or modality;
    directing the first carrier back to the transportation mechanism or modality of the LAS upon completion of the paraffin embedding; and
    reading the identification code and determining a subsequent location for the first carrier upon reentry of the carrier into the LAS transportation mechanism or modality, based upon the information originally inputted into the LAS.

3. The method of claim 2, further comprising the step of the LAS directing the carrier or specimen along the transportation mechanism or modality to an archiving station for storage of the first specimen, upon completion of all evaluations, processes and/or tests, the LAS removing the first specimen from calculations of priorities upon the directing of the carrier or specimen to the archiving station.

4. The method of claim 1, further comprising the steps of:
    providing a sensor at each workstation along the transportation mechanism or modality for reading the identification code on a carrier or specimen on the transportation mechanism or modality, the LAS being connected to each sensor for communication therewith;
    tracking a presence of a carrier or specimen at each sensor and identifying the carrier or specimen and location thereof.

5. The method of claim 1, further comprising the steps of:
    inputting the results of evaluations, processes and/or tests conducted on said first specimen or specimen into the LAS;
    updating its database with the first specimen tests results, and recalculating the priority of any additional evaluations, processes and/or tests to be conducted on the first specimen, in response to the updating of the database.

6. A method of routing a sample through an automated anatomic pathology laboratory system comprising:
    providing a plurality of tissue specimens in specimen carriers, each specimen carrier having a unique machine readable identifier;
    imputing information about each of the tissue specimens into a computer accessible database that is correlated to the unique machine readable identifier;
    placing the carriers in a receiving station;
    reading at least one of the unique machine readable identifiers;
    determining a priority for determining the order in which the tissue specimens are to be processed and/or tested, the processing and/or testing including a paraffin embedding process;
    determining a priority for one or more processes and/or tests to be performed on each tissue specimen;
    mechanically transporting via a transportation mechanism the tissue specimens to one or more workstations based on the priorities determined, the one or more workstations including at least a first paraffin embedding workstation disposed at a location immediately adjacent to the transportation mechanism.

7. The method of claim 6, wherein the unique machine readable identifier is an RFID device.

8. The method of claim 6, further comprising the step of recalculating the priority of one or more of the tissue specimens after transporting one or more of the tissue specimens to one of the workstations.

9. A method for routing an anatomic pathology specimen through an automated anatomic pathology system, comprising the steps of:
   entering a first anatomic pathology specimen to be evaluated, processed and/or tested in a specimen container;
   inputting information regarding the anatomic pathology specimen and the evaluation, processing and/or testing to be conducted on the anatomic pathology specimen into at least one of a computerized laboratory information system (LIS), an anatomic pathology information system (APIS) or an Electronic Health Record (EHR) ordering system, which is connected to and communicates with at least part of an anatomic pathology laboratory automation system (LAS) software;
   marking a first carrier and/or anatomic pathology specimen with an identification code identifying the first anatomic pathology specimen and the evaluation, processes and/or tests to be conducted thereon, the processes comprising a paraffin embedding process;
   placing the first anatomic pathology specimen in the first carrier and entering the first carrier into the LAS at a receiving station;
   reading the identification code and calculating:
   the priority of the first anatomic pathology specimen relative to any other anatomic pathology specimens entered into the LAS;
   the priority of each test to be conducted on the first anatomic pathology specimen thereof relative to one another; and
   the most direct route from the receiving station to a first paraffin embedding workstation for conducting the paraffin embedding process;
   entering the first carrier into the LAS by directing the carrier onto a transportation mechanism or modality of the LAS, the transportation mechanism or modality extending among a plurality of workstations, each workstation adapted to conduct a predetermined test;
   managing the transportation mechanism or modality to direct the first carrier and/or anatomic pathology specimen to the first paraffin embedding workstation;
   operating a gating mechanism at the first paraffin embedding workstation to direct the carrier to a workstation auxiliary transportation mechanism or conveyor, for embedding the anatomic pathology specimen in paraffin, the first paraffin embedding workstation disposed at a location immediately adjacent to the transportation mechanism; and
   recalculating the priority of the first anatomic pathology specimen and any other anatomic pathology specimens operating within the LAS upon directing of the first carrier or anatomic pathology specimen to the first paraffin embedding workstation.

10. The method of claim 9, further comprising the steps of:
    conducting the paraffin embedding after the step of directing the first carrier or anatomic pathology specimen to the first workstation auxiliary transportation mechanism or modality;
    directing the first carrier back to the transportation mechanism or modality of the LAS upon completion of the paraffin embedding; and
    reading the identification code and determining a subsequent location for the first carrier upon reentry of the carrier into the LAS transportation mechanism or modality, based upon the information originally inputted into the LAS.

11. The method of claim 10, further comprising the step of the LAS directing the carrier or anatomic pathology specimen along the transportation mechanism or modality to an archiving station for storage of the first anatomic pathology specimen, upon completion of all evaluations, processes and/or tests, the LAS removing the first anatomic pathology specimen from calculations of priorities upon the directing of the carrier or anatomic pathology specimen to the archiving station.

12. The method of claim 9, further comprising the steps of:
    providing a sensor at each workstation along the transportation mechanism or modality for reading the identification code on a carrier or anatomic pathology specimen on the transportation mechanism or modality, the LAS being connected to each sensor for communication therewith;
    tracking a presence of a carrier or anatomic pathology specimen at each sensor and identifying the carrier or anatomic pathology specimen and location thereof.

13. The method of claim 1, wherein the first specimen comprises a tissue specimen.

14. The method of claim 9, wherein the first anatomic pathology specimen comprises a tissue specimen.

* * * * *